United States Patent
Wallach et al.

(10) Patent No.: US 8,562,574 B2
(45) Date of Patent: Oct. 22, 2013

(54) CALLUS-TISSUE-DEBRIDEMENT APPARATUS

(76) Inventors: Gary S. Wallach, Fort Lauderdale, FL (US); Dario Nunez Ameni, Pittsburgh, PA (US)

( * ) Notice: Subject to any disclaimer, the term of this patent is extended or adjusted under 35 U.S.C. 154(b) by 383 days.

(21) Appl. No.: 12/900,807

(22) Filed: Oct. 8, 2010

(65) Prior Publication Data

US 2011/0060348 A1 Mar. 10, 2011

Related U.S. Application Data

(63) Continuation-in-part of application No. 11/860,511, filed on Sep. 24, 2007, now abandoned.

(60) Provisional application No. 61/377,798, filed on Aug. 27, 2010, provisional application No. 60/848,947, filed on Oct. 2, 2006.

(51) Int. Cl.
  *A61M 35/00* (2006.01)

(52) U.S. Cl.
  USPC .......... 604/293; 606/131; 132/73.6; 132/76.4

(58) Field of Classification Search
  USPC ........ 604/289–290, 293; 606/45, 131, 79, 81, 606/84, 85, 167–171; 132/73.6, 75.6, 75.8
  See application file for complete search history.

(56) References Cited

U.S. PATENT DOCUMENTS

| | | | |
|---|---|---|---|
| 4,241,499 A | 12/1980 | Perrone | |
| 4,380,549 A | 4/1983 | Van Scott et al. | |
| 4,589,994 A | 5/1986 | Moseman | |
| 4,608,370 A | 8/1986 | Aronsohn | |
| 4,708,873 A | 11/1987 | Schulte | |
| 5,082,009 A | 1/1992 | Cromer | |
| 5,505,948 A | 4/1996 | Rapaport | |
| 5,529,987 A | 6/1996 | Gallina | |
| 5,702,694 A | 12/1997 | Chamness | |
| 6,171,269 B1 | 1/2001 | Norin | |
| 6,178,970 B1 * | 1/2001 | Purifoy et al. | 132/76.4 |
| D448,119 S | 9/2001 | Neues | |
| 6,629,983 B1 * | 10/2003 | Ignon | 606/131 |
| 6,869,611 B1 | 3/2005 | Kligman et al. | |
| 6,916,297 B2 | 7/2005 | Hafemann | |
| 7,377,282 B2 * | 5/2008 | O'Dwyer | 132/73.6 |
| 7,581,545 B1 | 9/2009 | Moldawski et al. | |
| 7,615,239 B2 | 11/2009 | Santo et al. | |
| 8,066,013 B2 * | 11/2011 | Tes et al. | 132/73.6 |
| 8,226,662 B2 * | 7/2012 | Song | 606/131 |
| 2003/0005532 A1 | 1/2003 | Irizarry | |

(Continued)

OTHER PUBLICATIONS

Model 500 B Nail Dust Extractor and Drill System, Instruction Manual, Jan L Inc., Mar. 3, 2006.

(Continued)

*Primary Examiner* — Lynne Anderson
(74) *Attorney, Agent, or Firm* — Pate Peterson, PLLC; Warren M. Pate

(57) ABSTRACT

A system and method for debriding callus foot tissue is disclosed. The method may include applying a chemical peel to callus foot tissue and using a debriding tool to remove the chemically treated callus foot tissue. In certain embodiment, the method may include preparing the chemical peel, including customizing at least one attribute of the chemical peel based on at least one attribute of the callus foot tissue. The system may include a debriding tool having a cutting head that may be easily removed for cleaning or replacement.

17 Claims, 6 Drawing Sheets

(56) References Cited

U.S. PATENT DOCUMENTS

| | | |
|---|---|---|
| 2004/0162272 A1 | 8/2004 | Hansenne et al. |
| 2005/0084649 A1 | 4/2005 | Patlakh |
| 2005/0106116 A1 | 5/2005 | Smothers |
| 2007/0016118 A1 | 1/2007 | Kotlizky |
| 2007/0198031 A1 | 8/2007 | Kellogg |
| 2007/0283968 A1 | 12/2007 | Lee |

OTHER PUBLICATIONS

Espensen, Eric H., "Continuing Education: Assessing Debridement Options for Diabetic Wounds", (Mar. 2007).

"Wikipedia web page about chemical peels"—First accessed on Aug. 31, 2007.

Declaration of Gary S. Wallach executed Feb. 24, 2011.

* cited by examiner

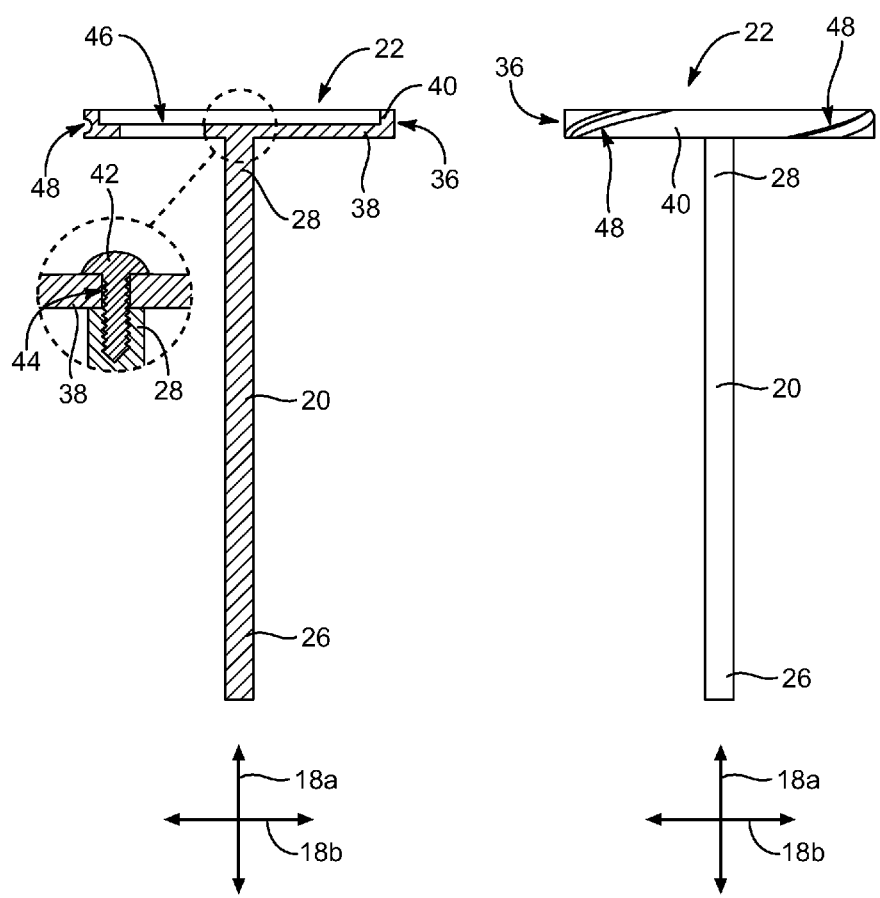

CALLUS-TISSUE-DEBRIDEMENT APPARATUS

RELATED APPLICATIONS

This application (1) claims the benefit of U.S. Provisional Patent Application Ser. No. 61/377,798 filed on Aug. 27, 2010 and (2) is a continuation-in-part of co-pending U.S. patent application Ser. No. 11/860,511 filed Sep. 24, 2007, now abandoned which claims the benefit of U.S. Provisional Patent Application Ser. No. 60/848,947 filed on Oct. 2, 2006.

U.S. patent application Ser. No. 11/860,511, U.S. Provisional Patent Application Ser. No. 60/848,947, and U.S. Provisional Patent Application Ser. No. 61/377,798 are each incorporated herein by reference.

BACKGROUND

1. The Field of the Invention

This invention relates to debridement and, more particularly, to novel systems and methods for removing callus foot tissue.

2. Background

Debridement is the removal of dead, damaged, or infected tissue. In the field of podiatry, standard debridement techniques typically include surgical removal of dead, damaged, or infected foot tissue, including callus foot tissue. Manual and powered instruments are commonly used for this purpose. For example, using standard podiatric techniques, a podiatrist may utilize a scalpel or other manual cutting tool to surgically cut or shave callus foot tissue, or a podiatrist may use a powered instrument such as a high-speed drill that spins a burr designed to surgically remove callus foot tissue.

However, conventional foot tissue debridement techniques have limitations. For example, simple, manual use of a scalpel to remove foot callus tissue is typically slow, painful, and prone to human error. Powered instruments can debride some foot tissue faster than manual instruments, but limitations remain. For example, great care must be used to avoid inflicting unnecessary pain, tearing tissue, and causing bleeding. In fact, certain burrs designed for abrasive debridement have been impractical, as well as unsuccessful in the market, namely because of their tendency to inflict pain, tear tissue, and cause bleeding. These limitations are especially problematic when working with thick, hardened, or fissured callus foot tissue.

Accordingly, the burrs commonly available in the modern market are in general limited to those designed for less abrasive and consequently less efficient debridement of foot tissue. The use of such burrs can require significant treatment times, especially when used to debride thick and hardened callus tissue. Moreover, such burrs tend to produce excessive amounts of fine particle dust when used on callus foot tissue.

The results produced by standard debridement techniques also leave room for improvement. For example, conventional surgical debridement of callus foot tissue may achieve a certain level of success in removing unwanted tissue, but success is limited by the nature and difficulty of working with (e.g., cutting, grinding, shaving, sanding, etc.) hardened callus foot tissue. Moreover, callus foot tissue that has been removed using standard debridement techniques often reforms at an unacceptable rate.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 5 is a side cross-sectional view of the shaft and flange of the debriding tool of FIG. 2;

FIG. 6 is a side elevation view of the shaft and flange of the debriding tool of FIG. 2;

DETAILED DESCRIPTION OF SELECTED EMBODIMENTS

Figure 1:
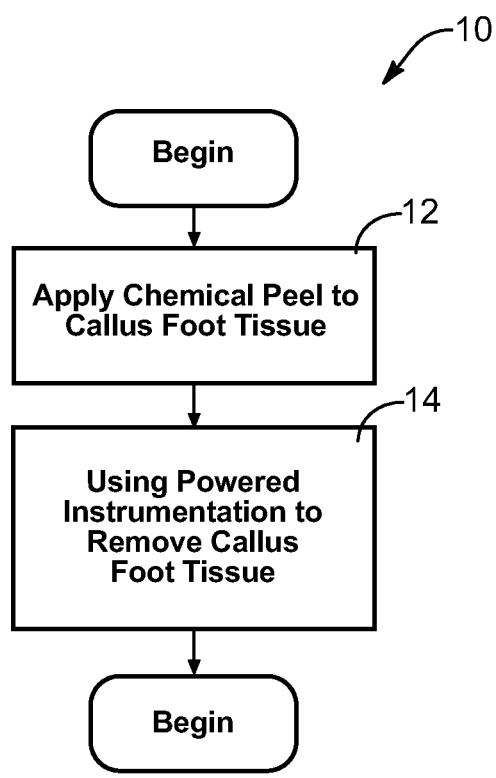
FIG. 1 is a schematic block diagram of one embodiment of a method for debriding callus foot tissue in accordance with the present invention.

It will be readily understood that the components of the present invention, as generally described and illustrated in the drawings herein, could be arranged and designed in a wide variety of different configurations. Thus, the following more detailed description of selected embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Exemplary embodiments of podiatric debridement are described herein. The embodiments are illustrative rather than restrictive. The embodiments described herein are described in relation to debridement of callus foot tissue. Callus foot tissue may include, but is not limited to, hardened foot tissue, excessively thick and hardened foot tissue, foot tissue having bleeding lesions, foot tissue having fissures, scaling tissue, corns, tyloma, hyperkeratosis, or other thickened, devitalized, or significantly keratinized tissue such as plaques or scales. Callus foot tissue may also include any other foot tissue where reduction of the tissue would be efficacious and beneficial (e.g., beneficial before initiation or application of other modalities, medications, or medical procedures).

The examples described herein have been found to generally debride callus foot tissue in an efficient, effective, and substantially pain-free manner. The exemplary processes described herein may reduce callus foot tissue remarkably more thoroughly, effectively, and efficiently than conventional debridement techniques. Thus, callus foot tissue may be efficiently removed or reduced to a degree that cannot be achieved by standard debridement techniques.

Moreover, the processes described herein typically reduce patient discomfort or pain as compared to standard debridement techniques. For example, the exemplary processes facilitate avoidance of, or at least significant and remarkable decreases in, instances of discomfort, pain, tissue tearing, and bleeding that may otherwise occur when standard debridement techniques are used.

Referring to FIG. 1, a method 10 of debriding callus tissue (e.g., callus foot tissue) is illustrated. In certain applications, the method 10 may be performed by a practitioner such as licensed professional (e.g., podiatrist) or a person acting under supervision of a licensed profession. While the illustrated method 10 may include exemplary acts or steps according to one embodiment, other embodiments may add to and/or modify any of the acts or steps shown.

In selected embodiments, a method 10 in accordance with the present invention may begin with the application 12 of a chemical peel to callus foot tissue. The chemical peel may be configured and used to chemically soften the callus foot tissue and may include one or more tissue debriding, softening, and/or desquamating agents capable of softening callus foot tissue. The chemical peel may include any suitable chemical composition that when applied will generally soften callus foot tissue, preferably in an efficient, safe, and controllable manner.

It will be appreciated that chemical treatment of callus foot tissue presents different considerations and challenges than chemical treatment of tissue on other parts of the body. On a histological level, a human foot includes more functional layers than other parts of the human anatomy. Moreover, callus foot tissue is often thicker and harder than callus tissue typically found on other parts of the body. Accordingly, the chemical peel used may be configured specifically for softening callus foot tissue in an efficient manner. For example, one or more agents in the chemical peel may have sufficient strength, potency, and/or concentration to efficiently effect satisfactory chemical penetration and/or softening on callus foot tissue.

Application 12 of the chemical peel may significantly soften the callus foot tissue. Such chemical softening of callus foot tissue is markedly different from merely moisturizing or hydrating skin using standard moisturizing or softening creams such as urea creams. Such creams cannot efficiently soften callus foot tissue in a manner that is acceptable for the exemplary methods disclosed herein. Moreover, the use of such standard creams typically requires a lengthy treatment period lasting days or weeks, as well as active patient compliance over the length of the treatment.

The chemical peel may include, but is not limited to, an alpha-beta peel, an alpha-beta peel mixture, or a chemical composition including one or more tissue softening agents configured to suitably soften callus foot tissue. Softening agents may include but are not limited to retinoic acid ("Retin-A"), lactic acid, glycolic acid, salicylic acid, alpha hydroxy acid ("AHA"), beta hydroxy acid ("BHA"), other acids capable of suitably softening callus foot tissue for the methods disclosed herein, and any suitable combination of such agents. In certain embodiments, the chemical peel may include desquamating agents such as salicylic acid.

The chemical peel may include one or more vehicular and/or penetrating agents such as dimethyl sulfoxide ("DMSO") for carrying the active ingredients (i.e., debriding agents) and/or penetrating the callus foot tissue. The chemical peel may include or be in the form of a surfactant with which any of the above-listed agents may be used.

Although not shown in FIG. 1, certain methods in accordance with the present invention may include preparing the chemical peel. Preparation of the chemical peel may be said to be an act that is performed separate from or as part of application 12 of the chemical peel to the callus foot tissue. Preparation of the chemical peel may include mixing together one or more ingredients such as tissue softening agents (e.g., alpha and beta acids) and vehicular and/or penetrating agents to form the chemical peel. For certain chemical peels to be effective, preparation of the peels should be performed just prior to their application rather than preparing the peels in advance.

Preparation of a chemical peel may include customizing the chemical peel (at least one attribute of the chemical peel) based on one or more factors, including, but not limited to, the treatment to be performed, patient preferences, and patient attributes (e.g., skin type, skin color, tissue hardness, tissue thickness, tissue location, tissue condition, etc.). In certain embodiments, for example, at least one attribute of the chemical peel is customized based on at least one attribute of the callus foot tissue (e.g., hardness, thickness, or location of the callus tissue). Attributes of the chemical peel that may be customized include, but are not limited to, the ingredients used in the chemical peel and the amount, concentration, and/or type of various ingredients such as softening and penetrating agents.

In certain embodiments, at least one attribute of the chemical peel may be adjusted based on a Fitzpatrick skin type score for a patient. Fitzpatrick skin type scores are well known. As an example, a higher concentration of an active ingredient (e.g., a tissue softening agent such as salicylic acid) may be used in a chemical peel to be applied to a skin type having a higher Fitzpatrick skin type score, while a lower concentration may be used for a skin type having a lower Fitzpatrick skin type score.

Other examples of customizing the chemical peel may include using stronger acids or concentrations of acids or other agents for softening especially thick or hard callus tissue, or using a higher concentration of penetrating agent such as DMSO to penetrate especially thick or hard callus tissue. In other words, the ingredients of the chemical peel may be adjusted as may best suit a particular treatment and/or skin condition (i.e., best debride or penetrate particular callus foot tissue).

Where a chemical peel is a mixture of ingredients, the ingredients may be combined together in any suitable manner, including using manual, automatic, or a combination of manual and automatic steps.

Chemical peels including salicylic acid in a range between approximately 50% and 70% in DMSO (5 mL), i.e., 500-700 mg of salicylic acid per one mL of DMSO, have been found to effectively and efficiently soften callus foot tissue. In certain examples, the concentration of the salicylic acid in DMSO may be adjusted between approximately 70% and 50% in DMSO (or other vehicular agent) to customize a chemical peel for a particular treatment, patient, skin type, etc. As mentioned, the customization may be based on one or more treatment-specific parameters such as the Fitzpatrick skin type score of a patient. Chemical peels including a mixture of approximately 20% glycolic acid in solution (5 mL), i.e., 200 mg for one mL of solution, have also been found to effectively and efficiently soften callus foot tissue.

A chemical peel may be applied to callus foot tissue in any suitable manner and using any potentially helpful tools. For example, one or more cotton swabs and/or cotton buds may be used to apply the chemical peel to callus foot tissue.

In selected embodiments, chemical peel may be applied 12 to one or more locations of a foot, including but not limited to a heel, ball, metatarsal area, sides, and toes of the foot. In certain embodiments, a method 10 may include selectively applying 12 the chemical peel to certain locations of a foot while avoiding application of the chemical peel to other locations on the foot. In certain examples, a method 10 may include applying 12 the chemical peel to callus foot tissue while avoiding application of the chemical peel to potentially sensitive areas of the foot such as on or near skin between toes or adjacent to the web space on the plantar surface of the foot.

The chemical peel may be permitted to work or act for a suitable period of time that allows for penetration of the chemical peel (or at least the active ingredients of the chemical peel) into, and sufficient softening of, the keratin of the callus foot tissue. Accordingly, applying 12 the chemical peel may include allowing sufficient time for the chemical peel to significantly soften the callus foot tissue. It has been found that waiting approximately four to five minutes generally allows for effective chemical penetration and softening of callus foot tissue. In certain embodiments, the waiting time is limited to a maximum of approximately four to five minutes.

In selected embodiments, the length of the waiting time for the chemical peel to soften tissue may be adjusted on a treatment-by-treatment basis, based on certain factors such as the thickness, hardness, and location of callus foot tissue. For example, the chemical peel may be allowed to soften tissue for a shorter period of time for callus tissue having a minimal thickness, or the waiting time may be extended for thicker or harder callus tissue.

In certain embodiments, applying 12 the chemical peel may include actively drying the chemical peel, or at least the top layer of the chemical peel, on the callus foot tissue. This may be accomplished using an electrically-powered fan. Other drying techniques and tools may be used, including applying heat (e.g., using a heat lamp or blow dryer) to dry the chemical peel. Actively drying the chemical peel can help speed up the treatment process.

Application 12 of the chemical peel may prepare callus foot tissue for effective and efficient debridement using instrumentation. In general, the callus foot tissue is significantly softened such that powered instrumentation can be used to remove the callus foot tissue efficiently, effectively, and in a generally pain-free manner. Typically, the results are remarkably improved as compared to results produced by standard podiatric debridement techniques.

Accordingly, a method 10 in accordance with the present invention may include using 14 instrumentation to remove the chemically softened callus foot tissue. Instrumentation may include any manual, powered, or combination of manual and powered instrumentation capable of surgically or physically debriding the chemically treated callus foot tissue.

In certain embodiments, a powered instrument producing a generally circular motion is used. For example, a powered drill with one or more cutting or buffing bits (e.g., burrs) may be used. The powered instrumentation may include a "Jan L" rotary powered nail drill with an RPM rating of approximately 25,000 to 30,000 with a dust extractor, or any powered instrument or system capable of producing powered motion of a disc, file, or other burr. For example, the powered instrument may include any powered drill that can accept the mandril of a suitable bit for debriding callus foot tissue. Suitable powered instruments developed in the future may also be used to drive a disc, file, drum, bit, or other burr useful for debriding callus foot tissue that has been softened by a chemical peel.

The powered drill may support using different bits. For example, a course bit such as a Cherokee circular disc (or other rotary flat-headed file) with multidirectional cutting teeth may be used to debride very thick and/or hardened callus tissue, and a less course bit such as a diamond circular burr (e.g., an "Umbrella" burr) may be used for callus foot tissue that is not as thick or hardened. The Cherokee circular disc may be used to remove thicker callus foot tissue. If the callus foot tissue is not very thick to begin with, or once the Cherokee circular disc has been used to remove the thick callus foot tissue, the diamond burr may be used to more gently buff the callus foot tissue. By supporting the use of variable bits, the powered instrumentation enables different degrees of powered cutting and/or buffing operations. Accordingly, using 14 instrumentation to debride the callus tissue may include sub-steps for different degrees and/or types of debriding.

By first softening callus foot tissue with a chemical peel, more aggressive (e.g., abrasive) tools may be used 14 than those typically used in standard surgical debridement techniques. For example, the Cherokee burr mentioned above has been a market failure at least in part because its abrasive qualities have been known to cause pain, tearing, and bleeding when used in standard surgical debridement techniques. Thus, this burr has been labeled as impractical for use in standard surgical debridement techniques. Remarkably, however, the burr has been found to perform efficiently, effectively, and in a substantially pain-free manner when used in the process of FIG. 1. Significantly, the chemical peel applied 12 efficiently softens callus foot tissue such that the Cherokee burr can be used 14 generally without inflicting pain, tearing skin, or causing bleeding.

In alternative embodiments, other suitable powered instrumentation may be used 14. In addition to circular debridement surfaces, other types of surfaces and/or motions may be employed by powered instrumentation to debride the callus foot tissue. For example, a rotating cylinder with a modified drill bit (e.g., a sanding drum with teeth) could be used 14. An oscillating bit such as a saw blade that moves forward and back may also be used 14. Yet another example includes using 14 a powered instrument that cuts in and out in the sagital plane (or up and down if the powered instrument is held on its side). Cross-cutting instrumentation may also be used 14.

The depth, speed, and area of removal of the callus foot tissue may be determined by the experience of the practitioner using 14 or directing the use 14 of the instrumentation. Application 12 of chemical peel and use 14 of instrumentation may be repeated for different layers of callus foot tissue, thereby allowing layer-by-layer removal of the callus foot tissue. For example, after application 12 of chemical peel and use 14 of instrumentation have removed one or more first layers of callus foot tissue, the steps 12, 14 may be repeated for one or more other layers (sub-layers) of the callus foot tissue. This is especially useful for treating very thick and hardened callus foot tissue as is commonly found on the bottom of human feet.

Other treatment options may be used to enhance a method 10 in accordance with the present invention. For example, pre-treatment of callus foot tissue using a standard podiatric debridement technique such as manual scalpel debridement may be used. By way of another example, a standard debridement technique may be used on callus foot tissue found at certain locations on a foot, including callus foot tissue on the dorsum of a toe, for example.

By using 14 powered instrumentation to debride callus foot tissue after the tissue has been chemically treated 12, a mini-scale, high speed debridement (e.g., cutting and/or buffing) of chemically treated callus foot tissue is performed. The mini-scale debridement in combination with the chemical treatment is able to remove callus foot tissue, without tearing at fissures of the callus foot tissue, which is a common problem of standard surgical debridement techniques. The combination of chemical treatment and powered debridement generally produces an efficient and pain-free process, in contrast to conventional debridement techniques.

It has been found that many treatments using methods 10 in accordance with the present invention may be performed in less than twenty minutes for both feet, without patients experiencing the human errors, pain, and discomfort that are commonly associated with standard debridement techniques.

Typically, the results produced by methods 10 in accordance with the present invention are remarkably improved as compared to results produced by standard podiatric debridement techniques. Tables 1-4 below include data representative of observed results produced by performance of the podiatric debridement processes described herein. Table 1 includes data for treatment of callus tissue on the heels of feet. Table 2 includes data for treatment of callus tissue on the balls of feet. Table 3 includes data for treatment of callus tissue on the toes of feet. Table 4 includes data for treatment of callus tissue on the marginal areas of feet.

As used herein for purposes of explaining the results produced by the practice of processes described herein, as represented by the data in Tables 1-4, the "heel" of a foot refers to the region of the foot formed by the calcaneus and that generally contacts the ground or footwear worn on the foot. The "ball" of a foot refers to the metatarsophalangeal area of the foot and the metatarsal arch. The "toes" of a foot refer to the plantar surfaces of the digits, the medial side of the hallux and the lateral side of the fifth toe. The "margin" of a foot refers to the lateral side of the foot from heel to metatarsophalangeal joint level.

In the results data of Tables 1-4, callus foot tissues have been categorized into four types based on attributes of the callus tissues. A podiatrist categorized the various callus foot tissues based on observation of the tissues. The four categories are: (1) excessive, thick callus tissue; (2) underlying fissure callus tissue; (3) bleeding lesion callus tissue; and (4) scaling skin callus tissue. The data for any of these categories included in a Table are also totaled in the Table.

The data in the Tables is representative of results produced by using the podiatric debridement processes disclosed herein to treat over one hundred different patients. The data is based on and representative of observations made by a podiatrist during post-treatment follow-up visits conducted approximately eight weeks after treatments were performed. The data in the Tables generally indicates an approximate percentage by which callus foot tissue has been reduced from its original condition. Thus, a "percent reduction" refers to the percentage by which callus foot tissue been reduced at approximately eight weeks after treatment, as compared to the original, pre-treatment state of the tissue. For example, a 75% reduction indicates that callus foot tissue at eight weeks post-treatment has been reduced by 75% as compared to its pre-treatment state.

In the Tables, the percentage reduction has been grouped into three different categories: "10% reduction," meaning approximately 10%-49% reduction; "50% reduction," meaning approximately 50%-74% reduction; and "75% reduction," meaning 75%-100% reduction.

TABLE 1

| Evaluation Heel: Type of Lesion | 10% Reduction | 50% Reduction | 75% Reduction |
|---|---|---|---|
| (1) Excessive, thick callus tissue | 28% | 47% | 25% |
| (2) Underlying fissure | 10% | 65% | 25% |
| (3) Bleeding lesion | 75% | 0% | 25% |
| Total: % for all heel lesion types | 25% | 50% | 25% |

Turning now to the Tables, Table 1 includes data related to the treatment of the heels of human feet. As shown in Table 1, for treatments of excessive, thick callus tissue on the heels of feet, 28% of the treatments produced a "10% reduction," 47% of the treatments produced a "50% reduction," and 25% of the treatments produced a "75% reduction." For treatments of underlying fissure callus tissue on the heels of feet, 10% of the treatments produced a "10% reduction," 65% of the treatments produced a "50% reduction," and 25% of the treatments produced a "75% reduction." For treatments of bleeding lesion callus tissue on the heels of feet, 75% of the treatments produced a "10% reduction," 0% of the treatments produced a "50% reduction," and 25% of the treatments produced a "75% reduction." For all treated categories of callus heel tissue, 25% of the treatments produced a "10% reduction," 50% of the treatments produced a "50% reduction," and 25% of the treatments produced a "75% reduction."

TABLE 2

| Evaluation Ball: Type of Lesion | 10% Reduction | 50% Reduction | 75% Reduction |
|---|---|---|---|
| (1) Excessive, thick callus tissue | 23% | 45% | 32% |
| (2) Underlying fissure | 33% | 0% | 67% |
| Total: % for all ball lesion types | 23% | 43% | 34% |

Table 2 includes data related to the treatment of the balls of human feet. As shown in Table 2, for treatments of excessive, thick callus tissue on the balls of feet, 23% of the treatments produced a "10% reduction," 45% of the treatments produced a "50% reduction," and 32% of the treatments produced a "75% reduction." For treatments of underlying fissure callus tissue on the heels of feet, 33% of the treatments produced a "10% reduction," 0% of the treatments produced a "50% reduction," and 67% of the treatments produced a "75% reduction." For all treated categories of callus tissue on the balls of feet, 23% of the treatments produced a "10% reduction," 43% of the treatments produced a "50% reduction," and 34% of the treatments produced a "75% reduction."

TABLE 3

| Evaluation Toes: Type of Lesion | 10% Reduction | 50% Reduction | 75% Reduction |
|---|---|---|---|
| (1) Excessive, thick callus tissue | 26% | 44% | 29% |
| Total: % for all toes lesion types | 26% | 44% | 29% |

Table 3 includes data related to the treatment of the toes of human feet. As shown in Table 3, for treatments of excessive, thick callus tissue on the toes of feet, 26% of the treatments produced a "10% reduction," 44% of the treatments produced a "50% reduction," and 29% of the treatments produced a "75% reduction." For all treated categories of callus tissue on the toes of feet, which includes only excessive, thick callus tissue in this set of data, the numbers are the same.

TABLE 4

| Evaluation Margins: Type of Lesion | 10% Reduction | 50% Reduction | 75% Reduction |
|---|---|---|---|
| (1) Scaling skin callus tissue | 20% | 80% | 0% |
| Total: % for all margins lesion types | 20% | 80% | 0% |

Table 4 includes data related to the treatment of the margins of human feet. As shown in Table 4, for treatments of scaling callus tissue on the margins of feet, 20% of the treatments produced a "10% reduction," 80% of the treatments produced a "50% reduction," and 0% of the treatments produced a "75% reduction." For all treated categories of callus tissue on the margins of feet, which includes only scaling callus tissue in this set of data, the numbers are the same.

Treatments of callus foot tissue using the processes disclosed herein produced remarkably improved results as compared to results typically produced by standard debridement techniques. In addition to efficiently and effectively debriding callus foot tissue in a generally pain-free manner, the data in the Tables shows that reoccurrences of debrided callus foot tissue are improved when compared to the results produced by standard debridement techniques. It has been observed by a podiatrist that callus foot tissue that has been debrided as described herein tends to reform after treatment but at reduced rates as compared with the return of callus foot tissue that has been treated using standard techniques.

In certain implementations, instruction for performing the above-described processes may be provided. Such instruction may include any direction for preparing a chemical peel configured to suitably soften callus foot tissue, applying the chemical peel to the callus foot tissue, using instrumentation to remove the chemically softened callus foot tissue, and performing any of the other acts described herein. The instruction may be provided in the form of in-person training, pre-recorded media (e.g., audio and/or visual instruction), print materials, seminars, classroom instruction, and any other suitable form. Along with instruction for performing the above-described podiatric debridement processes, at least one ingredient of the chemical peel and/or at least one component of the instrumentation (e.g., a burr) may be provided, thereby facilitating performance of the processes.

Figure 2:
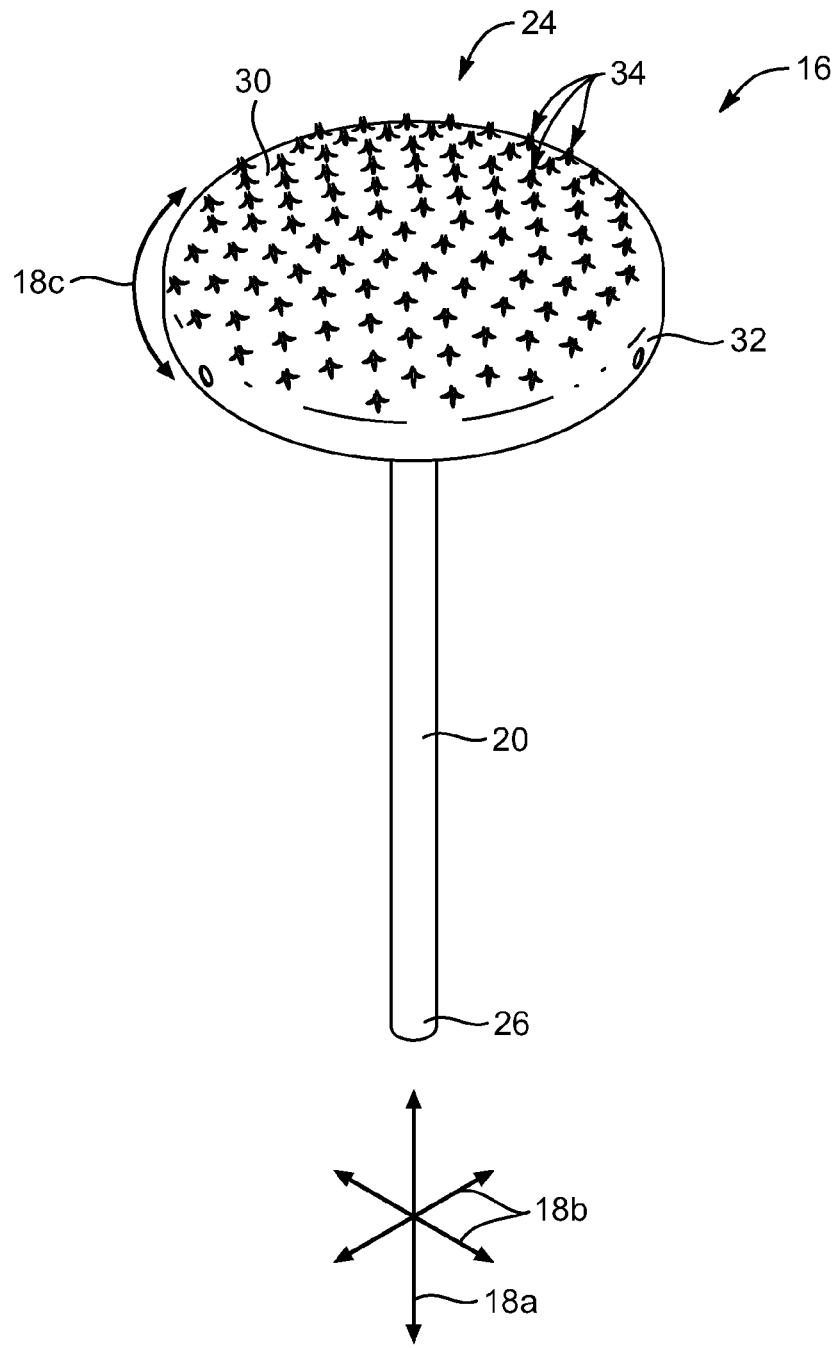
FIG. 2 is a perspective view of one embodiment of a debriding tool in accordance with the present invention.
Figure 3:
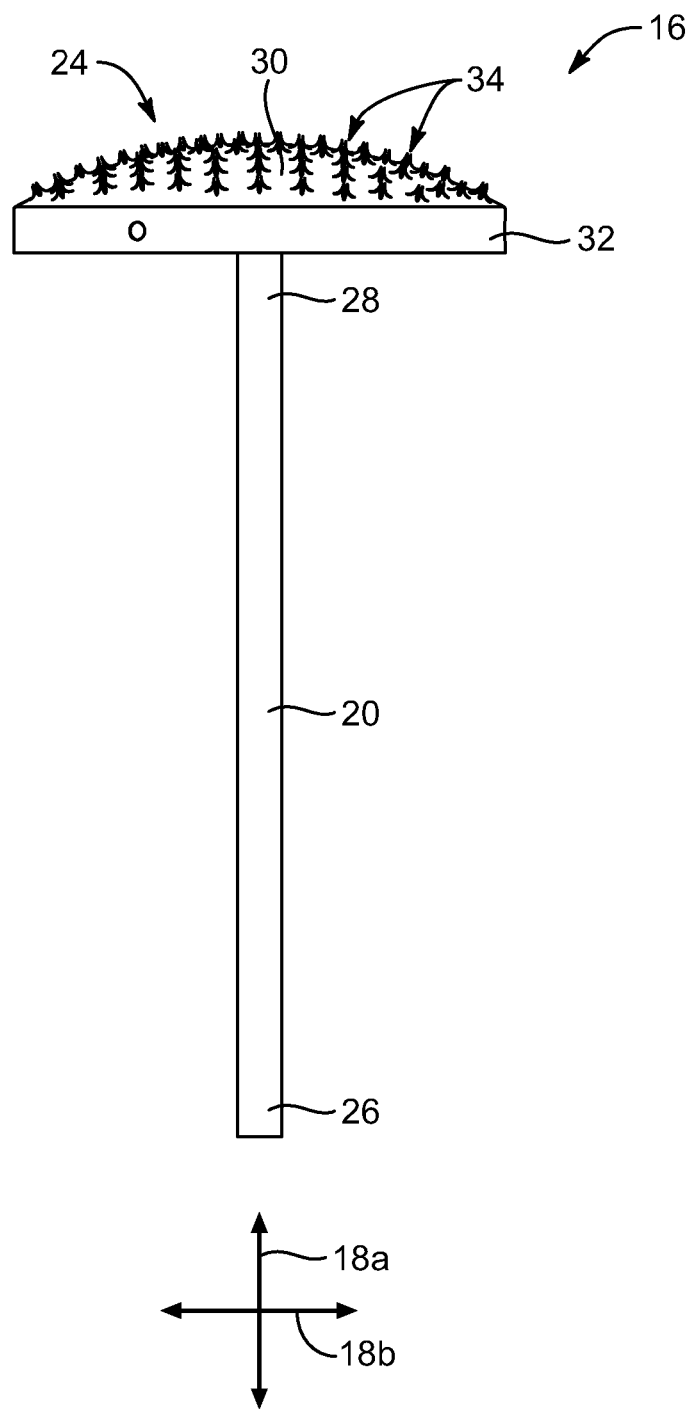
FIG. 3 is a side elevation view of the debriding tool of FIG. 2.
Figure 4:
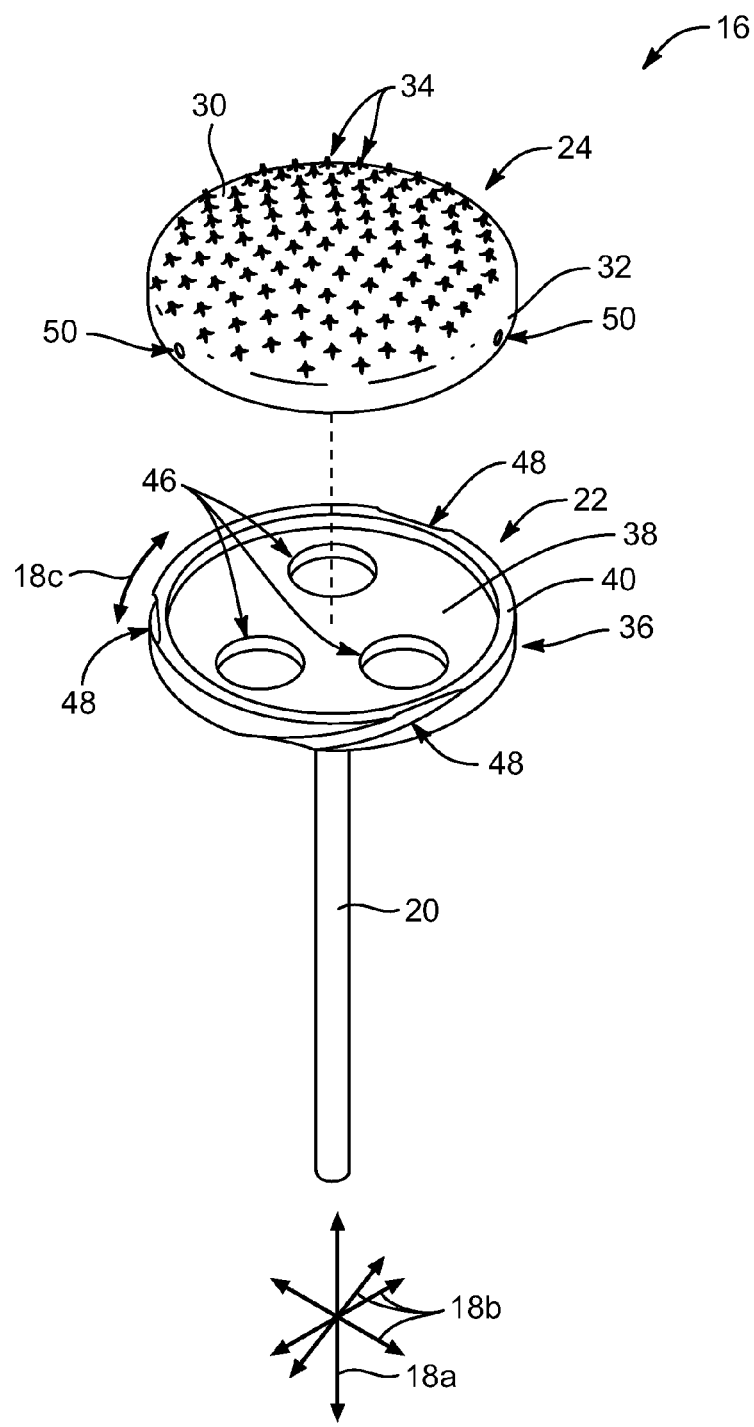
FIG. 4 is an exploded view of the debriding tool of FIG. 2.

Referring to FIGS. 2-4, in describing a debriding tool 16 in accordance with the present invention, it may be helpful to first establish various directions defined by such a tool 16. In selected embodiments, a debriding tool 16 may define an axial direction 18a, radial direction 18b, and circumferential direction 18c.

In certain embodiments, a debriding tool 16 may include or comprise a shaft 20, flange 22, and cutting head 24. A shaft 20 may extending in the axial direction 18a from a first end 26 to a second end 28. A first end 26 of a shaft 20 may be sized and shaped to facilitate engagement with a rotary instrument. For example, the first end 26 of a shaft 20 may be sized and shaped to fit the chuck of one or more rotary instruments.

A second end 28 of a shaft 20 may engage or be connected to a flange 22. A flange 22 may extend away from the second end 28 in a radial direction 18b. In selected embodiments, a flange 22 may form an interface between a shaft 20 and a cutting head 24. A cutting head 24 may be selectively removable from a flange 22. In certain embodiment, a cutting head 24 may be removed from a flange 22 to enable cleaning of the flange 22, the cutting head 24, or both. In other embodiments, a cutting head 24 may be removed and discarded after one or more uses. A new cutting head 24 may then be secured to a flange 22 for additional or sequent uses.

A cutting head 24 may include an end cap 30 and a side wall 32. An end cap 30 may include or support multiple burrs 34. Each such burr 34 in accordance with the present invention may comprise a cutting edge 34 or site 34, an abrading edge 34 or site 34, a cutting extension 34, or the like. A side wall 32 may provide the interface between an end cap 30 and a corresponding flange 22.

In selected embodiments, a flange 22 may be circular. In such embodiments, the end cap 30 may also be circular and have a circular perimeter. The side wall 32 may extend from the perimeter to cover a circumference 36 of the flange 22. Accordingly, in selected embodiments, a side wall 32 may comprise a cylindrical side wall 32.

A debriding tool 16 may be used 14 in methods 10 in accordance with the present invention. In operation, a first end 26 of a shaft 20 may be secured within the chuck of a rotary instrument. The rotary instrument may then rotate the tool 16 about an axis extending in the axial direction 18a. The speed of rotation set somewhere in the range from about 1,500 RPM to about 30,000 RPM, depending on various factors including the desired rate of tissue removal, skill of the practitioner, condition of the callus tissue, etc. Application of the end cap 30 and the associated burrs 34 to callus foot tissue (e.g., chemically softened callus foot tissue) may result in debridement of that tissue.

In selected embodiments, the side wall 32 of a cutting head 24 may be devoid of burrs 34. Such embodiments may reduce the likelihood of any burr 34 inadvertently contacting a patient or practitioner. That is, with the side wall 32 devoid of burrs 34, the practitioner may focus primarily on what is contacting the end cap 30 and with what force. Additionally, a side wall 32 devoid of burrs 34 may facilitate installation and removal of the cutting head 24 from a corresponding flange 22.

Referring to FIGS. 4-6, in certain embodiments, a flange 22 in accordance with the present invention may include a web 38 and a circumferential rib 40 or lip 40. The web 38 may extend radially 18b to connect a shaft 22 to the circumferential rib 40. A web 38 may be connected to a shaft 22 in any suitable manner. In selected embodiments, a shaft 22, web 38, and circumferential rib 40 may all be formed as a monolithic, seamless unit. For example, a shaft 22, web 38, and circumferential rib 40 may be turned from a single piece of stock metal. Alternatively, a web 38 may be connected to a shaft 22 by a fastener 42. For example, a fastener 42 may extend through an aperture 44 in the web 38 to engage (e.g., threadedly engage) the second end 28 of a shaft 22.

A web 38 may include one or more apertures 46 extending in the axial direction 18a therethrough. The apertures 46 may provide an exit location for tissue that has been removed from a patient. That is, as the burrs 34 of a cutting head 24 contact or move across the callus tissue of a patient, they may remove from the patient pieces of that callus tissue. Depending on the shape or configuration of the burrs 34, a portion (e.g., a majority) of those pieces may be drawn or deposited within a volume between a flange 22 and a cutting head 24. Accordingly, the apertures 46 may provide a location for the pieces to escape that volume.

In selected embodiments, a debriding tool 16 may be installed in a rotary instrument providing rotation of the tool 16, as well as collection of debris generated by the tool 16. For example, the rotary instrument may provide a suction and filtration system with an intake located proximate a tool 16 secured therein. In such embodiments, the apertures 46 may be sized and positioned to enable debris to pass therethrough directly into the collection system of the rotary instrument.

A circumferential rib 40 may include, form, or define the circumference 36 of a flange 22. Accordingly, a circumferential rib 40 may provide a structure facilitating engagement between a flange 22 and a corresponding cutting head 24. In selected embodiments, a circumferential rib 40 may be formed to include a structure for engaging and retaining a corresponding cutting head 24.

For example, in certain embodiments, a circumferential rib 40 may include one or more spiraling grooves 48. The grooves 48 may be formed to received extensions 50 formed in a corresponding cutting head 24. Accordingly, after a cutting head 24 has been aligned with a corresponding flange 22, rotation (i.e., rotation about an axis extending in the axial direction 18a) of the cutting head 24 with respect to the flange 22 may draw the cutting head 24 tightly against the flange 22 in a screw-thread-type engagement.

The direction in which the grooves 48 spiral around the circumference 36 of a flange 22 may depend on the direction of rotation to be imposed on the tool 16 by a corresponding rotary instrument. Typically, the grooves 48 may be configured such that the direction of rotation for securing a cutting head 24 may be opposite to the direction of rotation of the cutting head 24 during use. So configured, use of the cutting head 24 may tend to tighten the engagement between the cutting head 24 and the corresponding flange 22.

In selected alternative embodiments, the side wall 32 of a cutting head 24 may include one or more spiraling grooves. The grooves may be formed to receive one or more extensions formed on the circumference 36 of a corresponding flange 22. Accordingly, after a cutting head 24 has been aligned with a corresponding flange 22, rotation (i.e., rotation about an axis extending in the axial direction 18a) of the cutting head 24 with respect to the flange 22 may draw the cutting head 24 tightly against the flange 22 in a screw-thread-type engagement.

Once a cutting head 24 has been secured to a corresponding flange 22, the side wall 32 of the cutting head 24 may cover the circumference 36 (e.g., circumferential rib 40) of the flange 22. Accordingly, the cutting head 24 may comprise, include, or define the only surfaces likely to contact a patient, practitioner, or both.

Figure 7:
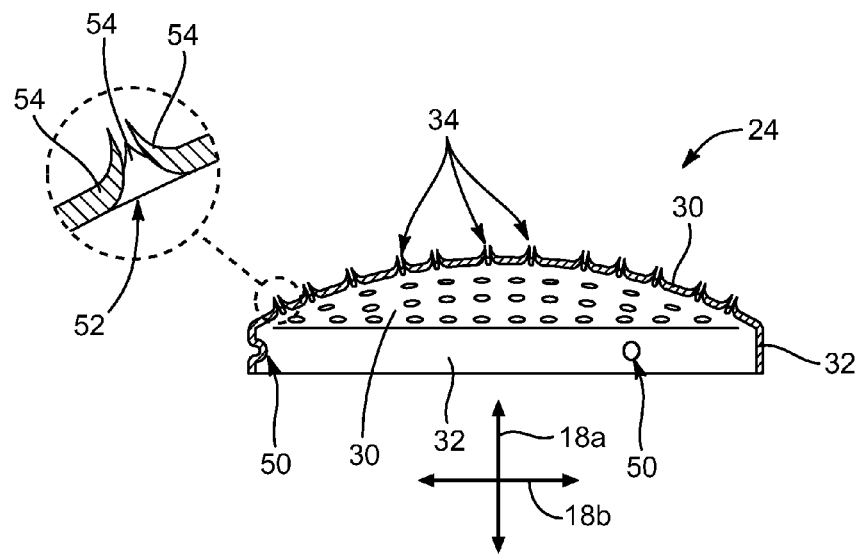
FIG. 7 is a side cross-sectional view of the cutting head of the debriding tool of FIG. 2.

Referring to FIG. 7, in selected embodiments, the one or more extensions 50 of a cutting head 24 may comprise one or more dimples 50 formed in the side wall 32. In some embodiments, the dimples 50 may be point or circular dimples 50. In other embodiments (not shown), the dimples 50 may be more elongated, spiraling dimples.

The number of extensions 50 formed in a cutting head 24 may correspond to the number of spiraling grooves 48 formed in a flange 22. In selected embodiments, a flange 22 may include three separate spiraling grooves 48 uniformly distributed about the circumference 36 of the flange 22. Accordingly, in such embodiments, a cutting head 24 may include three separate extensions 50 uniformly distributed about the side wall 32 of the cutting head 24.

A burr 34 in accordance with the present invention may have any suitable configuration. A burr 34 may remove tissue from a patient via cutting, abrasion, or the like, or some combination thereof. In selected embodiments, a burr 34 may provide multi-directional cutting or abrasion. For example, a burr 34 may remove tissue from a patient both while advancing and retreating.

In certain embodiments, a burr 34 may comprise a location where a punch has penetrated the material forming the cutting head 24 from the underside thereof. The penetration 52 and associated tearing or cutting caused by such a punch may produce one or more cutting edges 54 extending away from the rest of the cutting head 24. The number and shape of the cutting edges 54 associated with a particular penetration 52 may be controlled by the shape of the punch used to form the penetration 52, as well as the depth to which the punch is driven into or through the material forming the cutting head 24.

In selected embodiments, the end cap 30 of a cutting head 24 may have a convex or domed shape extending away from an underlying flange 22. A convex shape may enable a practitioner to better control the number of burrs 34 that engage the callus tissue of a patient as well as the force with which they do so. Additionally, a convex shape may enable a practitioner to reach callus tissue covering various hollows, indentations, concavities, or the like of the patient.

Figure 8:
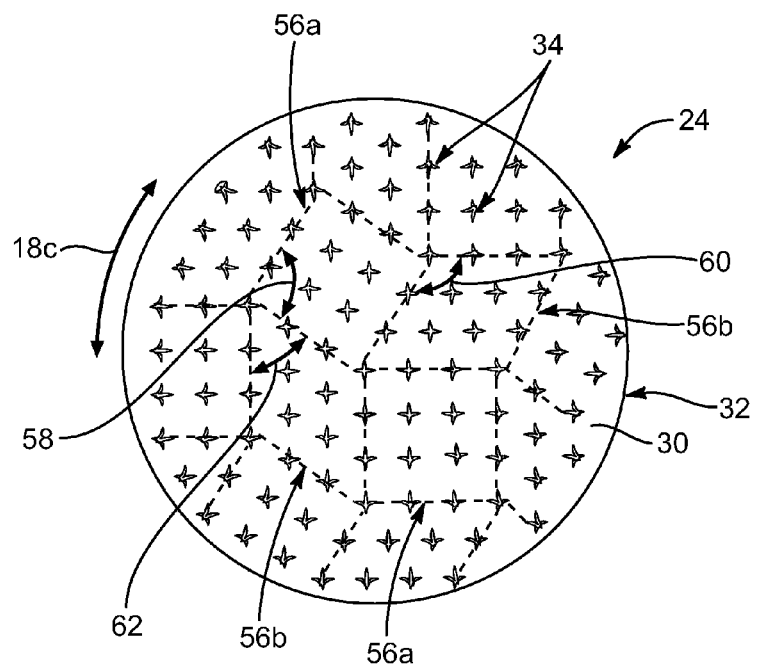
FIG. 8 is a top plan view of the cutting head of the debriding tool of FIG. 2.

Referring to FIG. 8, a cutting head 24 may include any suitable number of burrs 34 arranged in any suitable configuration. In selected embodiments, the burrs 34 may be arranged in groups of sixteen. The sixteen burrs 34 may be regularly distributed across the area of a parallelogram 56. Some of the resulting parallelograms 56a may be squares with corners 58 measuring ninety degrees. The other parallelograms 56b may comprise two corners 60 measuring one hundred twenty degrees and two corners 62 measuring sixty degrees. The various parallelograms 56a, 56b may be arranged such that each shares its sides (and corresponding burrs 34) with its four neighboring parallelograms 56a, 56b. The result may be a distribution of burrs 34 providing predictable and controllable removal of callus tissue.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A debriding tool defining axial, radial, and circumferential directions, the tool comprising:
   a shaft extending in the axial direction and having a first end and a second end opposite the first end in the axial direction;
   a flange connected to the second end of the shaft to extend in the radial direction therefrom;
   the flange defining at least one aperture extending in the axial direction therethrough;
   the flange having a circumference formed to including at least one spiraling groove; and
   a cutting head comprising
      a convex end cap,
      a cylindrical side wall,
      the convex end cap comprising a plurality of burrs,
      the cylindrical side wall extending from a perimeter of the convex end cap to cover the circumference of the flange, and
      the cylindrical side wall comprising at least one extension extending to engage the at least one spiraling groove to secure the cutting head to the flange.

2. The tool of claim 1, wherein the cylindrical side wall is devoid of burrs.

3. The tool of claim 2, wherein the at least one extension comprises a dimple formed in the cylindrical side wall.

4. The tool of claim 2, wherein the at least one spiraling groove comprises a first spiraling groove, a second spiraling groove, and a third spiraling groove uniformly distributed about the circumference of the flange.

5. The tool of claim 4, wherein the at least one extension comprises a first dimple, second dimple, and third dimple formed in the cylindrical side wall to be uniformly distributed thereon.

6. The tool of claim 5, wherein the first, second, and third extensions engage the first, second, and third spiraling grooves, respectively.

7. The tool of claim 1, wherein the shaft and flange are formed together as a monolithic, seamless unit.

8. The tool of claim 1, wherein the at least one aperture comprises three circular apertures extending in the axial direction through the flange.

9. The tool of claim 1, wherein the cutting head is selectively removable from the flange via rotation in a first direction about an axis extending in the axial direction.

10. A debriding tool defining axial, radial, and circumferential directions, the tool comprising:
a shaft extending in the axial direction and having a first end and a second end opposite the first end in the axial direction;
a flange connected to the second end of the shaft to extend in the radial direction therefrom;
the flange having a circumference and defining at least one aperture extending in the axial direction therethrough;
a cutting head comprising
a convex end cap comprising a plurality of burrs,
a cylindrical side wall devoid of burrs, and
the cylindrical side wall extending from a perimeter of the convex end cap to cover and engage the circumference of the flange; and
the cutting head being selectively removable from the flange via rotation in a first direction about an axis extending in the axial direction.

11. The tool of claim 10, wherein the cutting head further comprises at least one dimple formed in the cylindrical side wall.

12. The tool of claim 11, wherein the flange further comprises at least one spiraling groove formed in the circumference.

13. The tool of claim 12, wherein the at least one dimple engages the at least one groove to removably secure the cutting head to the flange.

14. The tool of claim 13, wherein the at least one spiraling groove comprises a first spiraling groove, a second spiraling groove, and a third spiraling groove uniformly distributed about the circumference of the flange.

15. The tool of claim 14, wherein the at least one dimple comprises a first dimple, second dimple, and third dimple formed in the cylindrical side wall to be uniformly distributed thereon.

16. The tool of claim 15, wherein the first, second, and third extensions engage the first, second, and third spiraling grooves, respectively.

17. The tool of claim 10, wherein the at least one aperture comprises three circular apertures extending in the axial direction through the flange.

* * * * *